(12) United States Patent
Mariani et al.

(10) Patent No.: US 9,307,932 B2
(45) Date of Patent: Apr. 12, 2016

(54) SYSTEM AND METHOD FOR 3D GAIT ASSESSMENT

(75) Inventors: Benoît Mariani, Renens (CH); Kamiar Aminian, La Tour-de-Pelz (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 27 days.

(21) Appl. No.: 13/810,118

(22) PCT Filed: May 25, 2011

(86) PCT No.: PCT/IB2011/052269
§ 371 (c)(1),
(2), (4) Date: Jan. 14, 2013

(87) PCT Pub. No.: WO2012/007855
PCT Pub. Date: Jan. 19, 2012

(65) Prior Publication Data
US 2013/0123665 A1    May 16, 2013

(30) Foreign Application Priority Data

Jul. 14, 2010 (WO) .................. PCT/IB2010/053211

(51) Int. Cl.
A61B 5/117    (2006.01)
A61B 5/103    (2006.01)
(Continued)

(52) U.S. Cl.
CPC ............... *A61B 5/112* (2013.01); *A61B 5/1038* (2013.01); *A61B 5/6807* (2013.01); *A61B 5/6829* (2013.01); *A61B 5/7242* (2013.01); *A61B 2562/0219* (2013.01)

(58) Field of Classification Search
CPC ..................................................... A61B 5/112
USPC ......................................................... 600/595
See application file for complete search history.

(56) References Cited

U.S. PATENT DOCUMENTS 6,122,960 A    9/2000 Hutchings et al.

OTHER PUBLICATIONS

Negard, Controlled FES-assisted gait training for hemiplegic stroke patients based on inertial sensors, Nov. 18, 2009, pp. 1-167.*

(Continued)

*Primary Examiner* — Brian Szmal
(74) *Attorney, Agent, or Firm* — Nixon & Vanderhye PC

(57) ABSTRACT

The invention relates to a system and a method for assessment of walking and miming gait in human. The method is preferably based on the fusion of a portable device featuring inertial sensors and several new dedicated signal processing algorithms: the detection of specific temporal events and parameters, 5 optimized fusion and de-drifted integration of inertial signals, automatic and online virtual alignment of sensors module, 3D foot kinematics estimation, a kinematic model for automatic online heel and toe position estimation, and finally the extraction of relevant and clinically meaning-full outcome parameters. Advantageously including at least one wireless inertial module attached to foot, the system provides common spatio-temporal parameters (gait cycle time, stride length, and stride velocity), with the 10 advantage of being able to work in unconstrained condition such as during turning or running. It furthermore may provide original parameters for each gait cycle, both temporal (load, foot-flat and push duration) and spatial (foot clearance and turning angle), and their inter-cycles variability. The system and method according to the invention allows the assessment of various aspects of gait which have shown recently to be of premium importance in research and clinical field, including foot clearance, 15 turns, gait initiation and termination, running, or gait variability. The system may be light weight, easy to wear and use, and suitable for any application requiring objective and quantitative evaluation of gait without heavy laboratory settings.

17 Claims, 6 Drawing Sheets

Figure 1:
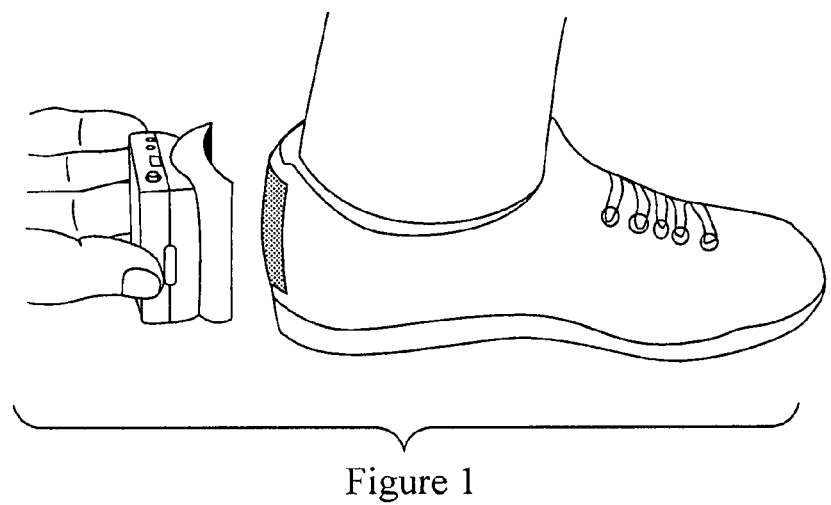

(51) Int. Cl.
*A61B 5/11* (2006.01)
*A61B 5/00* (2006.01)

(56) References Cited

OTHER PUBLICATIONS

International Search Report for PCT/IB2011/052269 mailed Oct. 18, 2011.
Written Opinion of the International Searching Authority mailed Oct. 18, 2011.
B. Mariani et al., "3D Gait Assessment in Young and Elderly Subjects Using Foot-Worn Inertial Sensors", Journal of Biomechanics, vol. 43, No. 15, Nov. 16, 2010, pp. 2999-3006.
T. Iris et al., "Results of Using a Wireless Inertial Measuring System to Quantify Gait Motions in Control Subjects", IEEE Transactions on Information Technology in Biomedicine, vol. 14, No. 4, Jul. 1, 2010, pp. 904-915.
D. Lai et al., "Measuring Toe Clearance Using a Wireless Inertial Sensing Device", Intelligent Sensors, Sensor Networks and Information Processing, 2008. ISSNIP 2008. International Conference, Dec. 15, 2008, pp. 375-380.
M. Benoit et al., "3D Gait Analysis Using Wearable 6D IMU on Shoe", Proceedings of the 19$^{th}$ Conference International Society for Posture and Gait Research, Jan. 1, 2009, pp. 47-48.
J. Van De Molengraft et al., "Wireless 6D Inertial Measurement Platform for Ambulatory Gait Monitoring", Proceedings of the 6th International Workshop on Wearable, Micro and Nanosystems for Personalised Health, Jun. 1, 2009, pp. 63-67.
H. Stolze et al., "Comparative Analysis of the Gait Disorder of Normal Pressure Hydrocephalus and Parkinson's Disease", J Neurol Neurosurg Psychiatry, Mar. 1, 2001, pp. 289-297.

\* cited by examiner

SYSTEM AND METHOD FOR 3D GAIT ASSESSMENT

This application is the U.S. national phase of International Application No. PCT/IB2011/052269 filed 25 May 2011 which designated the U.S. and claims priority to PCT/IB2010/053211 filed 14 Jul. 2010, the entire contents of each of which are hereby incorporated by reference.

1 FIELD OF INVENTION

The present invention relates to the assessment of gait (walking or running) through the use of at least one sensor fixed to the foot

2 STATE OF THE ART

In clinical setting, gait and mobility is commonly evaluated using questionnaire, observation or simple functional performance assessments (Tinetti, 1986; Podsiadlo and Richardson, 1991). These evaluations do not require sophisticated equipments and have the advantage of being easy to perform by trained evaluators. However, they are often subjective and dependant on the experience of evaluator. Furthermore, these measures do not allow evaluating specific spatio-temporal gait parameters that have been associated with frequent geriatric syndromes, such as falls, dementia, or frailty (Hausdorff et al., 2001; Kressig et al., 2004; Seematter-Bagnoud et al., 2009). Generally, spatio-temporal gait analysis requires dedicated laboratories with complex systems such as optical motion capture. Recently, ambulatory devices have overcome some of these limitations by using body-worn sensors measuring and analyzing gait kinematics. Unlike standard optical motion capture that requires a dedicated working volume, body worn sensors can be linked to a light data-logger carried by the subject performing his activities outside the lab with minimal hindrance. Nevertheless, recorded data require appropriate algorithms to compute relevant parameters for clinical use (Aminian, 2006).

Most common gait parameters, such as stride length or gait cycle time, can be obtained from the analysis of foot kinematics. Systems based on Micro-Electro-Mechanical Systems (MEMS) gyroscopes and accelerometers suffer from measurement errors and integration drifts, which limits position and orientation assessment during long-term measurements. However, by placing sensors on foot, drift can be corrected periodically by assuming null velocity of foot during foot-flat period of stance (Curey et al., 2004). Using this hypothesis, Sabatini et al. (2005) proposed a 2-Dimensional (2D) analysis method with periodic linear drift correction at each stance, and Bamberg et al. (2008) used a similar approach with wireless hardware. However, both studies were restricted to analysis in sagittal plane. Subsequently, Sabatini (2005) used a 3-Dimensional (3D) approach using quaternion for foot orientation and position. Veltlink et al. (2003) suggested a method for 3D foot kinematics estimation using ambulatory device for drop-foot stimulator with drift and azimuth resetting at each step. Using additional force sensors, Schepers et al. (2007) applied similar algorithms, focusing on foot placement in forward and lateral directions. Yet, these previous studies were limited to few subjects and the proposed methodologies were not evaluated against any reference instrumentation or only in "optimal" conditions, i.e. during straight walking. Some other studies have been published to track position wearing additional magnetometers (Yun et al., 2007) and/or GPS (Foxlin, 2005), but results remain essentially qualitative and were not validated for use in clinical field.

3 GENERAL DESCRIPTION OF THE INVENTION

The present invention relates to a method and a wearable system based on inertial sensors and dedicated algorithms for precise and accurate assessment of 3D gait spatio-temporal parameters.

In one preferred embodiment of the invention the method is based on temporal parameters detection coupled to an optimized fusion of inertial signals.

The invention offers the opportunity to assess 3D gait features outside lab.

Foot clearance and turning angle are two parameters which may be (separately or simultaneously) used in the present invention.

Foot clearance, defined as the foot's height during the swing phase, appears to be an important gait parameter that should be related to the risk of falling. Contrary to other gait parameters, there is an unambiguous mechanism that links impaired foot clearance to falls. During walking, insufficient or fluctuations in foot clearance could lead directly to tripping, a major cause of fall in older people. Foot clearance encapsulates several aspects, notably toe and heel clearance, and their 3D trajectory in space during gait. The present invention allow extracting minimal and maximal values of toe and heel clearance that are particularly relevant for clinical gait evaluation.

Turning angle is defined as the relative change in azimuth (i.e. the projection of orientation in ground plane (XY)) between the beginning and the end of gait cycle. Previous studies have shown the computation of 3D Orientation of body segments from body-fixed sensors, nevertheless, this information is difficult to interpret from a clinical point of view. Turning Angle allows quantifying the amount of turning of the user at each stride with a single metric. It notably allows interpreting gait variability due to extrinsic factors such as a change in walking direction of a user wearing the system.

The invention also advantageously takes stance analysis into account. In clinical gait evaluation, stance phase is defined as the period of time where the foot is in contact with the ground. In normal gait, stance phase last approximately 60% of the total gait cycle, with a period of double limb stance followed by single limb stance (also referred as single support), and again double limb stance (Sutherland et al 1988). (Winter et al. 1990) has characterized healthy elderly gait changes by a longer flat-footed landing. It shows that the sub-part of stance phase where the foot is almost completely still on the ground (so called "foot-flat") is particularly relevant in clinical gait assessment.

If most of the studies have proven the suitability of ambulatory measurements with the obvious advantage that information can be reliably derived on a large amount of data collected in daily condition, there are still some important limits to the existing methods. In most of them, stance phase is considered a single block without any subdivision from heel-strike to Toe-off, making it impossible to assess aspects such as foot-flat duration. A technical and a clinical objective are also reached with the present invention:

As technical objective, it is aimed at extracting innerstance phases, notably foot-flat, from the precise detection of stance temporal events on foot inertial signals. Those suitable inertial features are hypothesized for each temporal event could be found in agreement with force measurements on a three-segment foot model.

As clinical objective, it is aimed at introducing new temporal parameters in gait assessment as potential outcome tools for clinical evaluations. It is assumed that healthy and patient populations can be discriminated by different stance strategies and foot-flat duration.

So the present invention also offers a precise and objective method to detect the events of stance phase and extract temporal metrics to address both said technical and clinical objectives.

The invention also offers the opportunity to design a method providing objective parameters during running, in order to support or reject the hypothesis that sport activity, and particularly running, should be prohibited for patient after hip replacement. To this effect the method consists in adapting the existing algorithm to extract running phases and kinematics by using only shoe-mounted sensors. In addition muscular activity is recorded via electromyography (EMG). EMG and signals from MEMS accelerometers and gyroscopes may be recorded by two synchronized Physilog™ system. The full 3D motion of runner's foot and EMG may then be studied in order to extract precise and reliable parameters that can be used to evaluate running performance, limp and coordination.

4 DETAILED DESCRIPTION OF THE INVENTION

Figure 2:
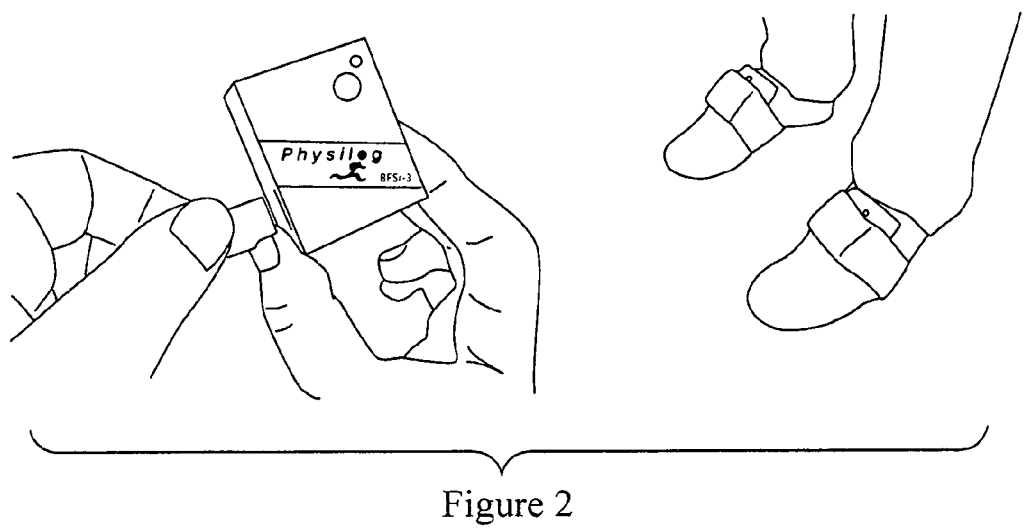
Figure 3:
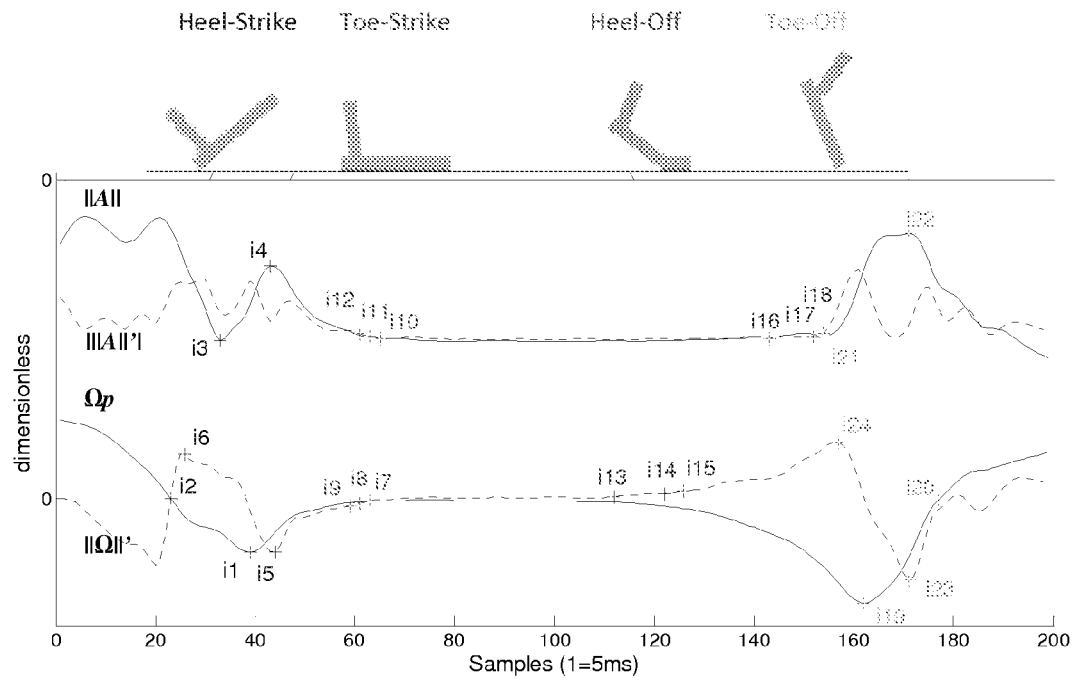

The invention will be better understood below by way of non-limitative examples and the following figures:

FIG. 1—S-Sense module with compliant foam attached with Velcro to hind part of shoe FIG. 2—"Physilog 3" Foot-worn sensors featuring 6DIMU and its fixation to user's shoes on forefoot FIG. 3—The inertial signals and the temporal events for one typical gait cycle and corresponding events. Inertial signals re scaled to be depicted together in one graph.

Figure 4:
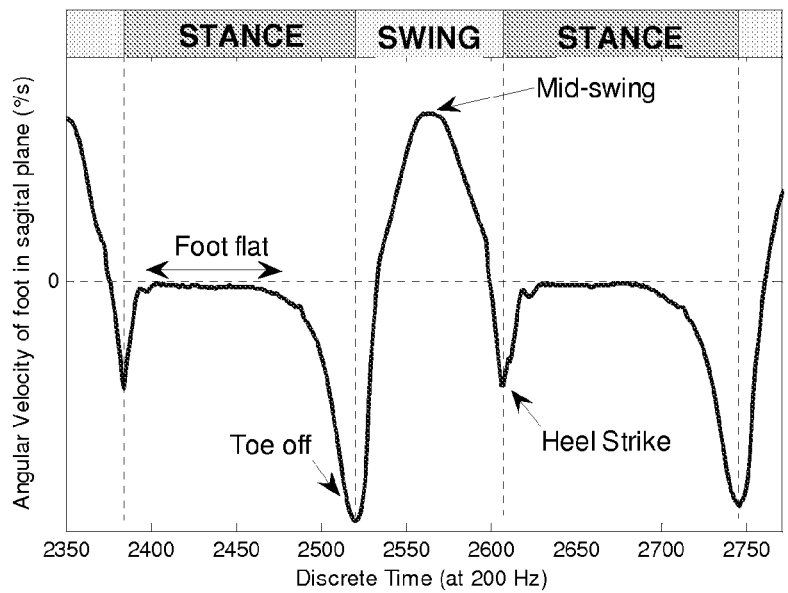

FIG. 4—Temporal phases

Figure 5:
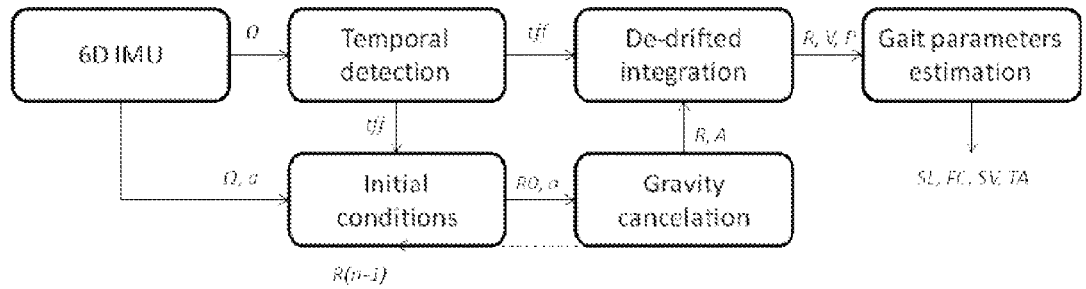

FIG. 5—Block Diagram of 3D Gait Analysis Algorithm

Figure 6:
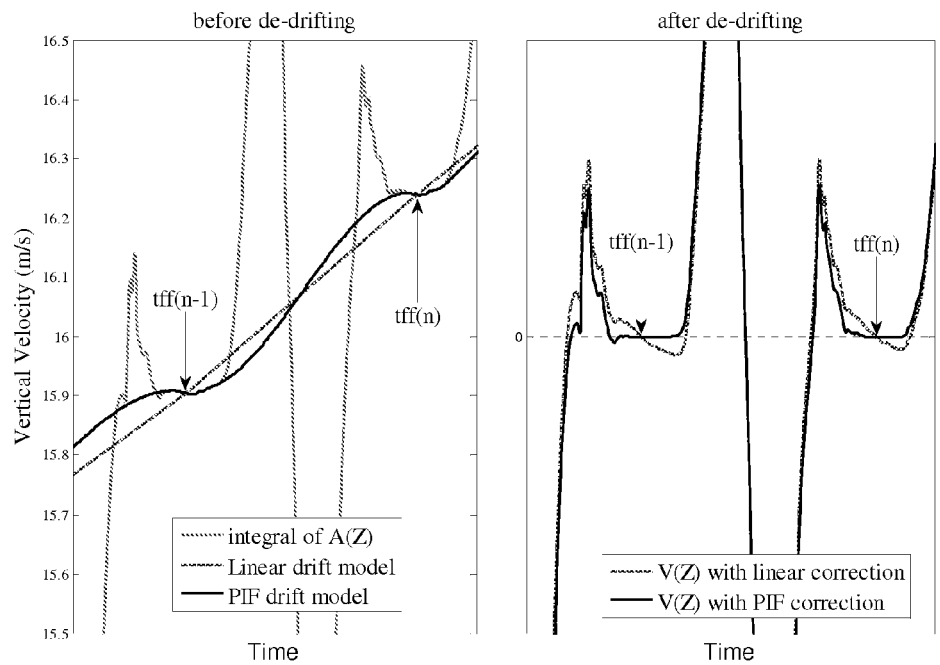

FIG. 6—De-drifted integration of vertical acceleration (A) to obtain vertical velocity (V) using linear function versus p-chip interpolation function (PIF)

Figure 7:
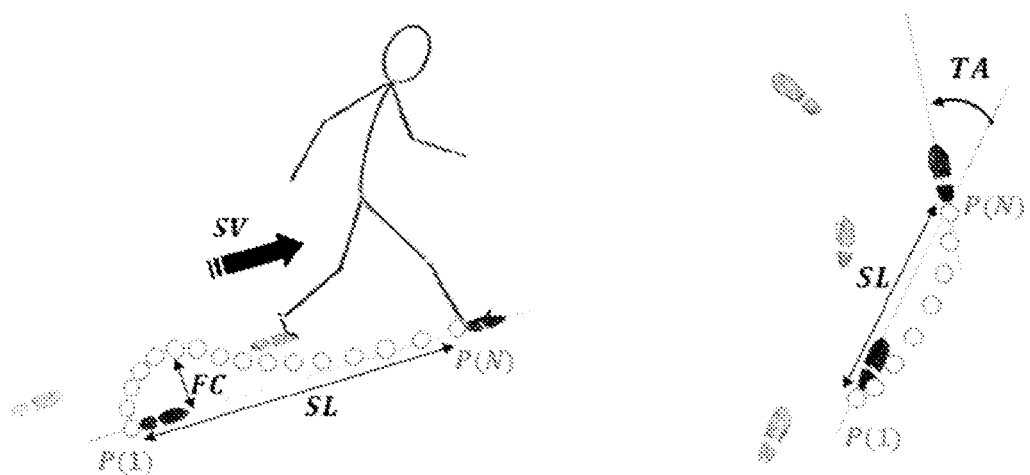

FIG. 7—3D Gait parameters estimation from 3D foot position (P) and azimuth (θ): Stride Length (SL), Stride Velocity (SV), Foot clearance (FC) and Turning Angle (TA).

Figure 8:
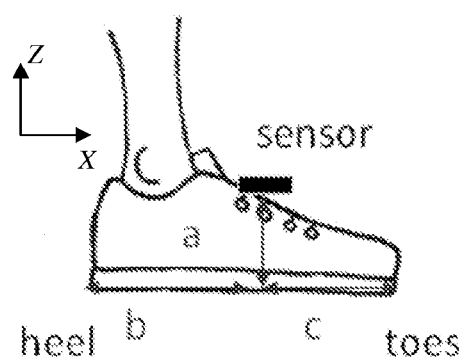

FIG. 8—Sensor relative position to heel and toes

Figure 9:
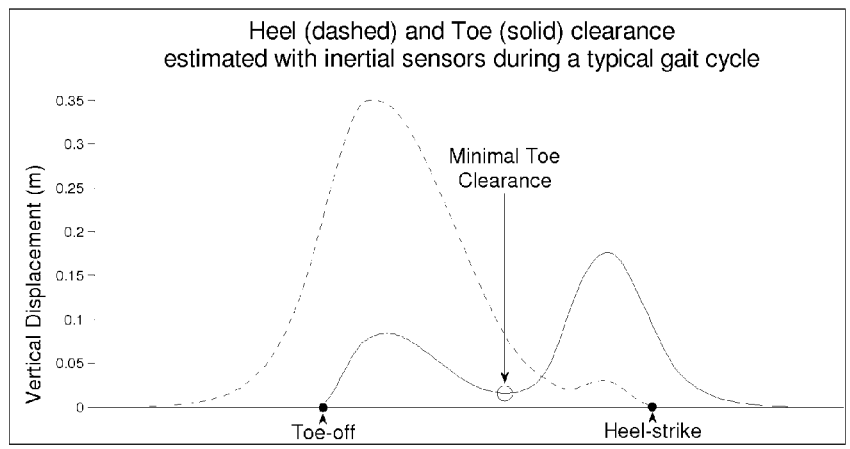
Figure 10:
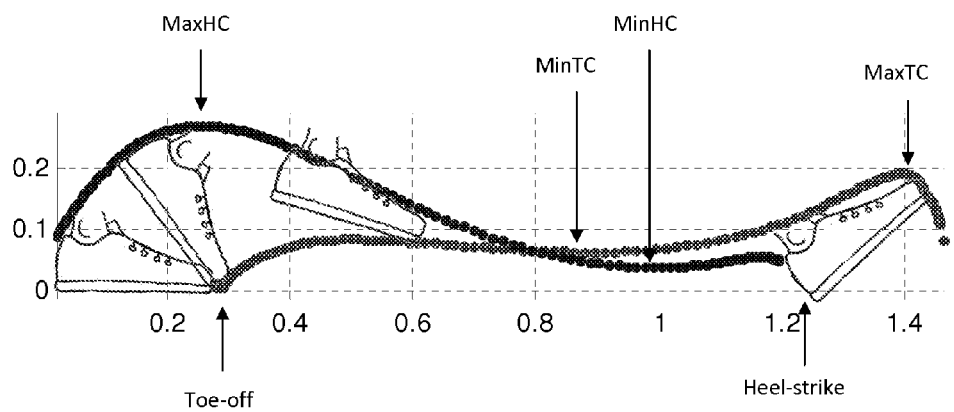
Figure 11:
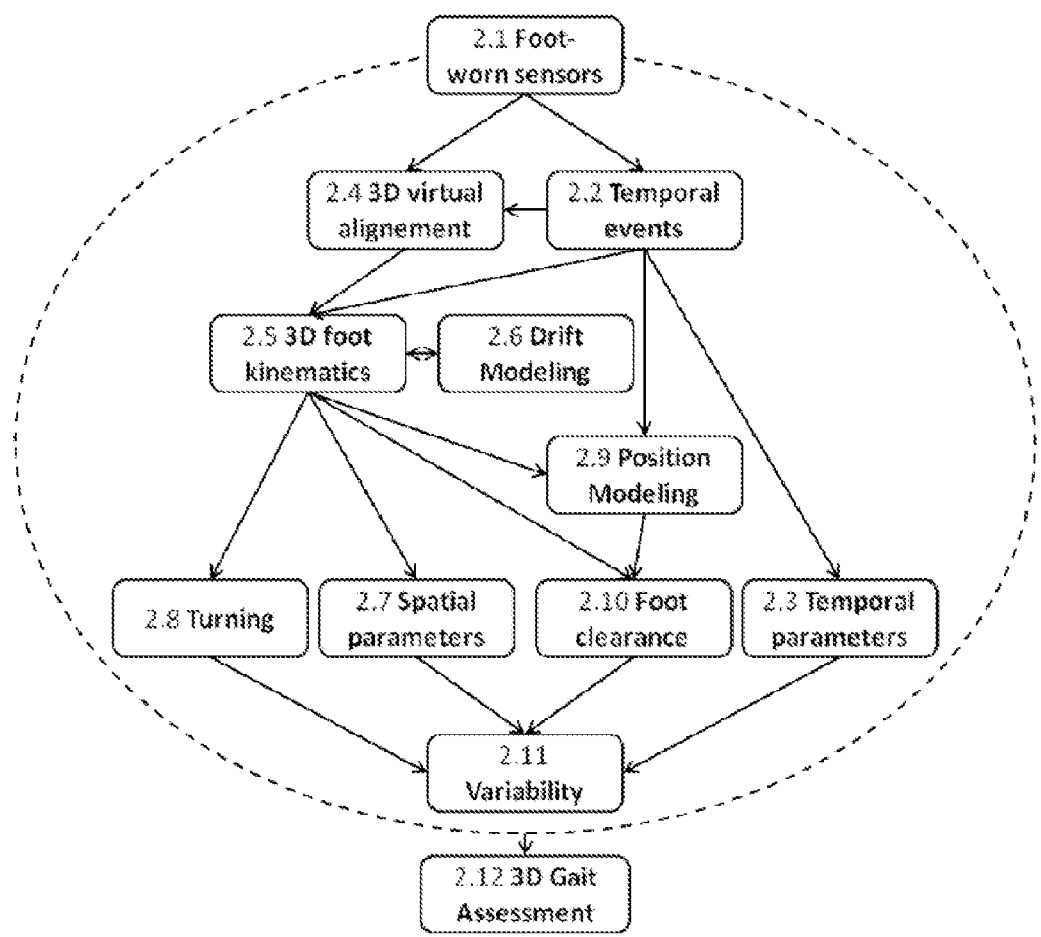

FIG. 9—Heel and Toe clearance estimation obtained from inertial sensors and kinematic model FIG. 10—Heel (*) and Toe (*) trajectory estimated by foot worn sensor system during a typical gait cycle FIG. 11—Sub-components of the invention and their interactions

4.1 FOOT-WORN SENSORS

A wireless 6 Dimensional-Inertial Measurement Unit (6D-IMU) referred as "S-Sense" has been designed (Van de Molengraft et al., 2009). S-Sense module is a small (57×41× 19.5 mm$^3$) and low power (18.5 mA@3.6V) stand-alone unit integrating microcontroller, radio transmitter, memory, three-axis accelerometer (ADXL, Analog Device, range 3 g), three-axis gyroscope (ADXRS, Analog Device, roll, yaw with 300 deg/s range, pitch with 800 deg/s range), and batteries, and can also feature datalogger recording on flash memory cards such as SD-card. S-Sense modules can be fixed on shoes at hind foot position using a compliant foam structure and double sided Velcro straps (FIG. 1).

Raw sensor data was low-pass filtered at 17 Hz, sampled on 12 bits at 200 Hz, and wirelessly transmitted in real time to a PC using "S-Base" receiver plugged in USB. In another embodiment of the invention, sample rate can be lowered to 100 Hz and/or sampled with higher resolution. Signals from two S-Senses were synchronized by considering the absolute real time clock sent by the base station to each module at the start of recording. Raw data were preliminary processed to extrapolate some missing data due to wireless data loss or sensor's output saturation (Van de Molengraft et al., 2009). Data from the two feet were finally converted to physical units (g or °/s) using in-field calibration method (Ferraris et al., 1995).

More generally, the invention can use any equivalent sensor measuring 3D accelerations and 3D angular velocities on foot. For example, it can be a 6D-IMU module directly integrated in shoe. Another new wireless 3D gait analysis system was designed, the "Physilog 3" (FIG. 2), which is also small and lightweight and more conveniently worn on the front foot using shape-memory foam and Velcro bands, and contain an equivalent 6D-IMU.

In addition, the module might contain or be synchronized with additional sensors such as GPS receiver, force sensors, magnetometers, optical range sensors or EMG electrodes, providing extrinsic information.

4.2 TEMPORAL EVENTS

During normal walking gait, stance phase is the period between initial contact, referred as Heel-Strike (HS), and terminal contact, referred as Toe-Off (TO), with the ground. In addition, this period encapsulates the instant where toes touch the ground, referred as Toe-strike (TS), and the instant where the heel leave the ground, referred as Heel-Off (HO). We call the successive events of HS, TS, HO, and TO the "Inner-stance phase events". The two negative peaks on pitch angular velocity ($\Omega_p$) are known to be approximate estimates of Heel-strike and Toe-off events (Aminian, 2002). Those features have shown to be robust on a wide range of healthy and pathologic populations (Salarian, 2004) and were used to distinguish them (Aminian, 2004). Then, we determined a time window between these two peaks to find other features to detect HS and TO based on the norm of the accelerometer signal ($\|A\|$) and the norm of the gyroscope signal, i.e., angular velocity, ($\|\Omega\|$) where the Euclidian norm of a vector $X=[x_1, x_2, x_3]$ is defined as $\|X\|=\sqrt{(x_1^2+x_2^2+x_3^2)}$. Regarding the period between TS and HO events, it is characterized by a lower amount of movement since the ground applies a mechanical constraint to the foot, and it is so-called foot-flat period. Consequently, TS and HO features are detected using a threshold on derivative of angular velocity norm ($\|\Omega\|'$), on pitch angular velocity ($\Omega_p$), and the absolute value of the Jerk, indicated by the derivative of accelerometer signal's norm ($|\|A\|'|$). For all inertial signals, the use of the norm of 3D signals allows being independent of sensor placement on the foot, making it more repeatable and no specific calibration to align them with anatomical frames (Cappozzo, 1995) is required whereas the use of only pitch signal allow to use a single sensor configuration. Those entire hypotheses for detecting temporal events are illustrated in FIG. 3.

During running gait, foot kinematics can be slightly modified. Other robust features and thresholds were adapted consequently to detect temporal events.

Furthermore, temporal event detection also provides the static periods where no movement is sensed (typically when signal variations are bellow a defined threshold), referred as motion-less for those which occurs during stance phase. Finally, midswing event (MS) detected from positive peak of pitch angular velocity during swing provides a robust hypothesis for detecting gait cycle in any condition.

4.3 TEMPORAL PARAMETERS

Based on the detected temporal events, meaningful metrics (e.g. parameters) for clinical gait analysis can be defined (FIG. 4). Thereby, stance phase was defined as follow:

Stance=$t$(TO)−$t$(HS)

Where t( ) is the occurrence instant of each event. Subsequently, the three periods composing the stance phase were defined as follows:

Load=$t$(TS)−$t$(HS)

Foot-flat=$t$(HO)−$t$(TS)

Push=$t$(TO)−$t$(HO)

Furthermore, Swing time, gait cycle time, can also be calculated as follow:

Swing=$t$(HS$^{+1}$)−$t$(TO)

Gait cycle=$t$(HS$^{+1}$)−$t$(HS)(or $t$(TO$^{+1}$)−$t$(TO)etc. . . . )

In case the system is mounted on two feet, double support parameters can also be calculated using classical definition (Aminian, 2002). Absolute metrics are calculated in milliseconds, and relative metrics are calculated as percentage of the stance time or gait cycle time.

4.4 3D VIRTUAL ALIGNMENT

When foot-worn sensors are fixed on subject's foot, their relative orientation in space is unknown. 3D virtual alignment method consists in finding the initial orientation of the sensor, represented equivalently by a 3×3 Matrix or a quaternion or an axis angle. Initial 3D orientation of module is obtained by using 3D acceleration ($a_n$) as inclination during static periods (provided by temporal events for example), and azimuth was set at which maximized the variance of angular velocity signal around pitch axis of foot. This original method has the great advantage of not requiring any functional calibration or precise positioning of the sensor module on subjects foot.

4.5 3D FOOT KINEMATICS

During each gait cycle n, 3D orientation ($R_n$), velocity ($V_n$), and trajectory ($P_n$) of foot were estimated from inertial signals. Practically, this involves the temporal detection of cycles, the knowledge of initial conditions of position and orientation, the gravity cancellation of measured acceleration, and the de-drifted integration of g-free acceleration. Moreover, kinematics measured by sensors in xyz should be expressed in XYZ to be compared with reference. FIG. 5 illustrates the main algorithmic steps.

Initial conditions were updated for each cycle n at tff$_n$, where the foot was considered motion-less. Initial 3D orientation of sensor module (R0$_n$) was obtained by using 3D acceleration ($a_n$) as inclination (i.e. by aligning z axis with Z), and azimuth was set at the value derived from the orientation at last sample (N) of previous step ($R_{n-1}$(N))). It means the system can work with any terrain inclination, i.e. that the invention can also detect the initial conditions during walking in slopes, thus making it possible to analyze 3D foot kinematics in such situations. Gravity cancellation was achieved by aligning the accelerometers' axes (xyz) with fixed frame (XYZ) and subtracting gravity vector. From initial orientation R0$_n$, the orientation of the foot relative to fixed frame ($R_n$(i)) was updated at each time frame (i=1, 2, . . . , N) by a quaternion-based time integration of angular velocity vector $\Omega_n$ between two successive foot-flats (tff$_{n-1}$, tff$_n$) (Sabatini, 2005; Favre et al., 2008). At each time frame i of cycle n, using measured accelerations ($a_n$(i)), gravity-free component of acceleration in fixed frame ($A_n$(i)) can be summarized by (1).

$A_n(i)=a_n(i)*R_n(i)-g$, where $g=(0,0,1)$ (1)

Single and double-integration of gravity-free acceleration ($A_n$) allowed obtaining 3D velocity and position of foot at each gait cycle n. By assuming that foot velocity is null at each tff$_n$ (Curey et al., 2004), estimation of velocity ($V_n$) was obtained by trapezoidal integration of $A_n$ and Position ($P_n$) was finally deduced by simple trapezoidal integration of velocity ($V_n$).

4.6 DRIFT MODELING

Integration step which is performed at 2.5 is prone to drifting errors, due to various sources such as electronic noise or sensors non-linear behaviors. So in practice, to obtain acceptable performance for estimating 3D foot kinematics, system drift needs to be corrected. This can be done using a classic linear de-drifting at each gait cycle between two motion-less period. In a preferred embodiment of the invention, the drift is removed by subtracting a sigmoid-like curve modeled based on a p-chip interpolation function (Carlson and Fritsch, 1985). The p-chip interpolation function (PIF), is defined between the value of $A_{n-1}$(tff$_{n-1}$) and $A_n$(tff$_n$)), (FIG. 6). As it is illustrated in FIG. 6, it provides a better estimation of drift in the particular case of gait since it is proportional to the quantity of movement, thus allowing improvement of accuracy and precision of 3D foot kinematics.

4.7 SPATIAL PARAMETERS

From the 3D foot kinematics, in addition to the overall 3D foot trajectory, the following gait parameters were extracted at each cycle n for both reference system and Foot-worn sensors using (2), (3), (4) and (5), where N represent the last sample of cycle n:

Stride length (SL) was defined as the distance measured between two successive foot-flat positions of the foot. This calculation is valid for curved and turning path as well (Huxham et al., 2006).

$SL_n=|P_n(N)-P_n(1)|$ (2)

Foot clearance (FC) was defined as the maximal foot height during swing phase relative to the height at foot-flat:

$FC_n=\max(P_n(1),P_n(2),\ldots,P_n(N))-P_n(1)$ (3)

Stride velocity (SV) was considered as the mean value of foot velocity in ground plane (XY) during each gait cycle:

$SV_n=\mathrm{mean}(V_{n|XY}(1),V_{n|XY}(2),\ldots,V_{n|XY}(N))$ (4)

4.8 TURNING

Turning Angle (TA) was defined as the relative change in azimuth (i.e. the projection of orientation in ground plane (XY)) between the beginning and the end of gait cycle.

$TA_n=\theta_n(N)-\theta_n(1)$ where $\theta_n=R_{n|XY}$ (5)

Extracted spatial parameters and turning are illustrated in FIG. 7.

4.9 POSITION MODELING

Foot clearance provided by 2.7 gives general information which is dependent to sensor positioning on foot. Typically, a bigger FC is measured if sensor is on the heel compare to the case where sensor is on the foot. In order to be independent of sensor positioning, we design a method to automatically model sensor relative position to heel and toe, based on 3D foot kinematics and biomechanical assumptions. The relative position of sensor module in foot sagittal frame to the toe and heel of the subject can be represented by 3 variables (FIG. 8).

By combining the position of sensor (P), the knowledge of foot orientation (R) and shoe size and assuming that at Toe-off (TO) (respectively heel-strike (HS)), toe's (respectively heel's) vertical position is 0, {a,b,c} during gait for each cycle n were computed by solving the following analytical equations:

$$\begin{cases} P_{n|Z}(HS) + b - b*R_{n|Z}(HS) - a*R_{n|X}(HS) = 0 \\ P_{n|Z}(TO) + b - b*R_{n|Z}(TO) + c*R_{n|X}(TO) = 0 \\ a + c = ShoeSize \end{cases}$$

4.10 FOOT CLEARANCE

Knowing sensor trajectory ($P_{sensor}$) and orientation (R) and relative position to heel and toe ({a,b,c}), heel clearance (HC) and toe clearance (TC) can be estimated by the following trigonometric relations:

$$HC = P_{sensor} + b - b*R_Z - a*R_X$$

$$TC = P_{sensor} + b - b*R_Z + c*R_X$$

In addition to FC, parameters such as Minimal Toe Clearance (MTC) can be extracted from heel and toe clearance at each gait cycle as illustrated in FIG. 9.

Other parameters such as MaxHC, MinHC, MaxTC or other statistical measures can be extracted from clearance curves according to FIG. 10.

4.11 VARIABILITY

Since subjects are not always performing pure straight walking, direct variability of gait observed can be due to the turning at the end of the pathway. So in order to focus on the assessment of the 'intrinsic dynamics' of continuous, normal walking, we need to ensure that the analysis is not influenced by those atypical strides outliers. Detection and correction of outliers in gait parameters series consists of the following steps:
- detect the gait cycles during turning, i.e. when TA is above a threshold obtained empirically
- replace turning gait cycle parameter with its median value during straight walking or simply remove it from the analysis.
- apply statistical method such as three-sigma rule to the new series in order to remove outlier related to other origins such as data loss or walking breaks (facultative)

To further quantify the stride-to-stride fluctuations in walking, there are various tools including commonly used linear parameters as well as non-linear methods. Parameters time series can be Foot clearance, Stride Length, Stride Velocity, Gait Cycle Time, or any other spatio-temporal parameter provided by the invention and previously described methods.

4.11.1 Linear Parameters

TABLE I

NOTATIONS

| Symbol | Quantity |
|---|---|
| s | gait parameter time series (can be Foot clearance, Stride Length, Stride Velocity, Gait Cycle Time) |
| $m_s$ | mean of s |
| $m_d$ | mean of the first derivative of s |
| $\sigma_s^2$ | variance of s |
| $\sigma_s$ | standard deviation of s |
| $\sigma_d$ | standard deviation of the first derivative of s |
| $\sigma_{dd}$ | standard deviation of the second derivative of s |
| Coefficient of variation: | $CV_s(\%) = \dfrac{\sigma_s}{m_s} \times 100$ |
| Burstiness parameter: | $B_s = \dfrac{\sigma_s - m_s}{\sigma_s + m_s}$ |
| Median Absolute Deviation (MAD): | $MAD_s = median(\|s - median(s)\|)$ |
| Standard deviation of the first derivative gait/stride time series: | $\sigma_d$ (SD1) |
| Interquartile range of the second derivative gait/stride time series: iqr1 | |
| Hjorth Complexity parameter: | $C_H = \dfrac{\sigma_{dd}\sigma_s^2}{(\sigma_d)^2}$ |
| Signal Permutation (Turns) Counts (STC) | |

In a given time series a data sample can be identified as a 'signal permutation/turn' (Note that 'turn' is not related to walking turn/outliers!) if it satisfies the following two criteria: 1) it represents an alteration of direction in the signal, i.e., a change in the sign of the derivative and 2) the difference (absolute value) between its amplitude and that of the preceding sample should be greater than a specific threshold. The number of signal permutation/turns in a time series represents the degree of signal variability.

4.11.2 Non-Linear Parameters: Stride-to-Stride Variability Analysis

The CV and related linear variability parameters quantify the magnitude of stride-to-stride variability but are not sensitive to changes in the ordering of the stride times or the dynamics Randomly reordering a time series will not affect the magnitude of the variability but may dramatically alter the dynamic properties. To quantify how the dynamics fluctuate over time during the walk, fractal DFA analysis and symbolic entropy measures are applied to the stride time series.

4.12 3D GAIT ASSESSMENT

In a preferred embodiment of the invention all previously discussed parameters are taken into consideration for the 3D Gait assessment. The system may provide objective evaluation of walking and running gait performance of a subject through original parameters such as foot clearance, foot-flat duration etc. . . . , in any sort of walking situation or test. The diagram of FIG. 11 gives an overview of the interactions between the subcomponents of a system including all those parameters.

5 FINAL COMMENTS

The invention differs from the prior art in that it uses a least one original parameter (either temporal or spatial) that can be measured when performing any gait activity. It allows assessment during straight and curved trajectory, during outdoor locomotion, in ramp, stairs or even during running. A new drift compensation method renders the system more robust for precise and accurate gait assessment despite errors due to the sensors. These extracted parameters show promising preliminary discriminative performance, as it was possible to distinguish young and elderly subjects. The system according to the present invention was used successfully in more than 600 elderly subjects. It may be used for various purposes such as clinical gait evaluation, performance assessment in athletes, functional tests in patient with gait impairments, treatment follow-up, etc. . . . For other application such as long-term tracking or clinical research however, it could require to be coupled with additional sensors such as magnetometers, GPS, EMG electrodes etc. . . .

The method according to the invention can be applied with sensor worn on any foot position.

Compared to other inertial-based gait analysis system (Aminian et al., 2002; Salarian et al., 2004; Sabatini et al., 2005; Schepers et al., 2007), similar or slightly better accuracy and precision was obtained for SL and SV. The method also provides stride-to-stride variability of gait, with the advantage of being able to extract outliers due to turning or other extrinsic variation that can be measured from the system. In controlled environments, previous studies showed significant associations between gait variability and various syndromes associated with aging, such as frailty (Seematter-Bagnoud et al., 2009), and fear of falling (Rochat et al., 2010).

The method according to the invention allows the analysis of curved trajectories, and provides new parameters such as TA and FC, which were not provided by any previous inertial-based system. Actually, TA is an important outcome to evaluate gait in Parkinson disease (Zampieri et al.) and FC, which was shown to be the most discriminative parameters between young and elderly subjects in our study, could also be an important new gait parameter to estimate risk of fall in elderly (Begg et al., 2007; Lai et al., 2008).

Finally, the system according to the invention is lightweight and can be worn directly on user's casual shoes or barefoot, thus minimizing intrusiveness and interference with normal gait conditions. It could also be directly integrated in the foot-wear. The system can be used as an objective tool in many applications requiring gait evaluation in real conditions without usual constraints of limited space due to laboratory settings.

The invention is of course not limited to the examples discussed previously.

1. REFERENCES

Aminian, K., Najafi, B., Bula, C. J., Leyvraz, P. F., Robert, P., 2002. Spatio-temporal parameters of gait measured by an ambulatory system using miniature gyroscopes. Journal of Biomechanics 35, 689-699.

Aminian, K., 2006. Monitoring Human Movement with Body-Fixed Sensors and its Clinical Applications. Invited chapter in "Computational intelligence for movement sciences: neural networks and other emerging techniques". Idea Group Pub., p. 101-138.

Bamberg, S. J. M., Benbasat, A. Y., Scarborough, D. M., Krebs, D. E., Paradiso, J. A., 2008. Gait analysis using a shoe-integrated wireless sensor system. IEEE Transactions on Information Technology in Biomedicine 12, 413-423.

Begg, R., Best, R., Dell'Oro, L., Taylor, S., 2007. Minimum foot clearance during walking: Strategies for the minimisation of trip-related falls. Gait and Posture 25, 191-198.

Bland, J. M., Altman, D. G., 1986. Statistical methods for assessing agreement between two methods of clinical measurement. Lancet 1, 307-310.

Carlson, R. E., Fritsch, F. N., 1985. MONOTONE PIECE-WISE BICUBIC INTERPOLATION. SIAM Journal on Numerical Analysis 22, 386-400.

Crapo, R. O., Casaburi, R., Coates, A. L., Enright, P. L., MacIntyre, N. R., McKay, R. T., Johnson, D., Wanger, J. S., Zeballos, R. J., Bittner, V., Mottram, C., 2002. ATS statement: Guidelines for the six-minute walk test. American Journal of Respiratory and Critical Care Medicine 166, 111-117.

Curey, R. K., Ash, M. E., Thielman, L. O., Barker, C. H., 2004. Proposed IEEE inertial systems terminology standard and other inertial sensor standards. In Proceedings of the Record—IEEE PLANS, Position Location and Navigation Symposium, 83-90.

Favre, J., Jolles, B. M., Aissaoui, R., Aminian, K., 2008. Ambulatory measurement of 3D knee joint angle. Journal of Biomechanics 41, 1029-1035.

Ferraris, F., Grimaldi, U., Parvis, M., 1995. Procedure for effortless in-field calibration of three-axis rate gyros and accelerometers. Sensors and Materials 7, 311-330.

Foxlin, E., 2005. Pedestrian tracking with shoe-mounted inertial sensors. IEEE Computer Graphics and Applications 25, 38-46.

Giansanti, D., 2006. Does centripetal acceleration affect trunk flexion monitoring by means of accelerometers? Physiological Measurement 27, 999-1008.

Hausdorff, J. M., Rios, D. A., Edelberg, H. K., 2001. Gait variability and fall risk in community-living older adults: A 1-year prospective study. Archives of Physical Medicine and Rehabilitation 82, 1050-1056.

Huxham, F., Gong, J., Baker, R., Morris, M., Iansek, R., 2006. Defining spatial parameters for non-linear walking. Gait and Posture 23, 159-163.

Kressig, R. W., Gregor, R. J., Oliver, A., Waddell, D., Smith, W., O'Grady, M., Curns, A. T., Kutner, M., Wolf, S. L., 2004. Temporal and spatial features of gait in older adults transitioning to frailty. Gait and Posture 20, 30-35.

Kuipers, J. B., 1999. Quaternions and rotation sequences. Princeton Univ. Press, p. Lai, D. T. H., Begg, R. K., Taylor, S., Palaniswami, M., 2008. Detection of tripping gait patterns in the elderly using autoregressive features and support vector machines. Journal of Biomechanics 41, 1762-1772.

Luinge, H. J., 2002. Inertial sensing of human movement. PhD. thesis, Twente University Press, Enschede, p.

Menz, H. B., Latt, M. D., Tiedemann, A., Kwan, M. M. S., Lord, S. R., 2004. Reliability of the GAITRiteÂ® walkway system for the quantification of temporo-spatial parameters of gait in young and older people. Gait and Posture 20, 20-25.

Podsiadlo, D., Richardson, S., 1991. The timed 'Up and Go': A test of basic functional mobility for frail elderly persons. Journal of the American Geriatrics Society 39, 142-148.

Sabatini, A. M., 2005. Quaternion-based strap-down integration method for applications of inertial sensing to gait analysis. Medical and Biological Engineering and Computing 43, 94-101.

Sabatini, A. M., Martelloni, C., Scapellato, S., Cavallo, F., 2005. Assessment of walking features from foot inertial sensing. IEEE Transactions on Biomedical Engineering 52, 486-494.

Salarian, A., Russmann, H., Vingerhoets, F. J. G., Dehollain, C., Blanc, Y., Burkhard, P. R., Aminian, K., 2004. Gait assessment in Parkinson's disease: Toward an ambulatory system for long-term monitoring. IEEE Transactions on Biomedical Engineering 51, 1434-1443.

Schepers, H. M., Koopman, H. F. J. M., Veltink, P. H., 2007. Ambulatory assessment of ankle and foot dynamics IEEE Transactions on Biomedical Engineering 54, 895-902.

Seematter-Bagnoud, L., Santos-Eggimann, B., Rochat, S., Martin, E., Karmaniola, A., Aminian, K., Piot-Ziegler, C., Bula, C. J., 2009. Vulnerability in high-functioning persons aged 65 to 70 years: The importance of the fear factor. Aging Clin Exp Res Tegner, Y., Lysholm, J., Lysholm, M., Gillquist, J., 1986. A performance test to monitor rehabilitation and evaluate anterior cruciate ligament injuries. American Journal of Sports Medicine 14, 156-159.

Tinetti, M. E., 1986. Performance-orientated assessment of mobility problems in elderly patients. Journal of the American Geriatrics Society 34, 119-126.

Van de Molengraft, J., Nimmala, S., Mariani, B., Aminian, K., Penders, J., 2009. Wireless 6D inertial measurement platform for ambulatory gait monitoring. In Proceedings of the Proceedings of the 6th international workshop on Wearable, Micro and Nanosystems for Personalised Health, Oslo, Norway, 63-64.

Veltink, P. H., Slycke, P., Hemssems, J., Buschman, R., Bultstra, G., Hermens, H., 2003. Three dimensional inertial sensing of foot movements for automatic tuning of a two-channel implantable drop-foot stimulator. Medical Engineering and Physics 25, 21-28.

Von Eye, A., Mun, E. Y., 2006. Analyzing rater agreement: Manifest variable methods. Applied Psychological Measurement 30, 154-156.

Winter, D. A., Patla, A. E., Frank, J. S., Walt, S. E., 1990. Biomechanical walking pattern changes in the fit and healthy elderly. Physical Therapy 70, 340-347.

Yun, X., Bachmann, E. R., Moore Iv, H., Calusdian, J., 2007. Self-contained position tracking of human movement using small inertial/magnetic sensor modules. In Proceedings of the Proceedings—IEEE International Conference on Robotics and Automation, 2526-2533.

Rochat, S., Büla, C. J., Martin, E., Seematter-Bagnoud, L., Karmaniola, A., Aminian, K., Piot-Ziegler, C., Santos-Eggimann, B., 2010. What is the Relationship Between Fear of Falling and Gait in Well-Functioning Older Persons Aged 65 to 70 Years? Archives of Physical Medicine and Rehabilitation, 91 (6), pp. 879-884.

Zampieri, C., Salarian, A., Carlson-Kuhta, P., Aminian, K., Nutt, J. G., Horak, F. B., 2010. The instrumented timed up and go test: Potential outcome measure for disease modifying therapies in Parkinson's disease. Journal of Neurology, Neurosurgery and Psychiatry 81, 171-176.

The invention claimed is:

1. A method of 3D gait assessment, the method comprising:
   obtaining, using at least one inertial sensor fixed to the foot or integrated on a shoe, a turning foot parameter and a clearance foot parameter, the clearance foot parameter being based on calculated heel clearance and toe clearance values;
   quantifying said turning foot parameter during gait from a spatial orientation of the foot and temporal events, including turning angle; and
   applying a sensor fusion and foot kinematics algorithm on the obtained parameters in performing the 3D gait assessment;
   wherein at least one of a GPS receiver, force sensor, magnetometer, optical range sensor, and EMG electrode is synchronized with the at least one inertial sensor to provide extrinsic information.

2. The method according to claim 1, wherein the obtaining comprises variability measurement of each obtained parameter.

3. The method according to claim 1, further comprising deriving temporal foot parameters from temporal events of gait detected by said sensor(s), said temporal events being based on mathematical transformation of angular velocity and acceleration signals and including active or static periods, heel-strike, toe-strike, motion-less, heel-off, toe-off, and mid-swing.

4. The method according to claim 3, wherein the deriving is based on function generation between said temporal events for modeling, and compensating for inertial sensors drift.

5. The method according to claim 1, further comprising deriving temporal foot parameters from temporal events of gait detected by said sensor(s), said temporal events being based on at least one of: load, foot-flat, push, swing and stance duration, as well as double-support when each foot has an associated sensing module.

6. The method according to claim 1, further comprising determining 3D foot kinematics, including position and orientation, during human gait locomotion, including any one or more of: straight walking; turning; walking on uneven terrain, stairs, or a ramp; and running.

7. The method according to claim 1, further comprising extracting spatial foot parameters at each gait cycle from temporal events and foot kinematics, including 3D foot trajectory, stride length, stride velocity, and foot clearance.

8. The method according to claim 1, further comprising using a kinematic model that provides positions of heel and toe during gait from a combination of temporal events and the trajectory of another point on foot.

9. The method according to claim 1, further comprising quantifying said clearance foot parameter from spatial trajectories of the sensor(s), heel, or toe during gait at each cycle, including minimum and maximum of toe and heel clearance.

10. The method according to claim 1, further comprising taking into consideration the stride-to-stride variability of a gait parameters time series in removal of turning outliers.

11. The method of claim 1, wherein the algorithm includes:
   during each gait cycle, estimating from inertial signals received from at least one 6 degree of freedom inertial sensor 3D orientation, velocity, and trajectory of the foot, based on:
      temporal detection of cycles,
      knowledge of initial conditions of position and orientation,
      gravity cancellation of measured acceleration, and
      de-drifted integration of gravity-free acceleration; and
   using the estimated 3D orientation, velocity, and trajectory of the foot in order to estimate gait parameters including stride length, foot clearance, stride velocity, and turning angle.

12. A wearable system for 3D gait assessment, comprising:
   at least one inertial sensor to be fixed to a foot or integrated on a shoe, wherein at least one of a GPS receiver, force sensor, magnetometer, optical range sensor, and EMG electrode is synchronized with the at least one inertial sensor to provide extrinsic information, wherein the at least one sensor is configured to measure a turning foot parameter and/or a clearance foot parameter, the clearance foot parameter being based on calculated heel clearance and toe clearance values, and said turning foot parameter being quantifiable during gait from a spatial orientation of the foot and temporal events, including turning angle, and further comprising:

an output configured to provide the obtained parameters to a processing device configured to apply a sensor fusion and foot kinematics algorithm thereon to perform the 3D gait assessment.

13. The system according to claim 12, further comprising a 6 degree of freedom inertial sensor.

14. A method comprising:
providing the wearable system of claim 12;
performing a 3D alignment of said system relative to user's gait frame; and
using the wearable system for 3D gait assessment.

15. The system of claim 12, wherein the at least one sensor is further configured to provide output to a computer-controlled module that applies a sensor fusion and foot kinematics algorithm on the measured parameter(s) in performing 3D gait assessment.

16. A method of 3D gait assessment, the method comprising:
obtaining, using at least one inertial sensor fixed to the foot or integrated on a shoe, at least one of a turning foot parameter, a spatial foot parameter, a clearance foot parameter, and a temporal foot parameter; and
applying a sensor fusion and foot kinematics algorithm on the obtained parameter(s) in performing the 3D gait assessment,
wherein the obtaining comprises variability measurement of each obtained parameter,
wherein at least one of a GPS receiver, force sensor, magnetometer, optical range sensor, and EMG electrode is synchronized with the at least one inertial sensor to provide extrinsic information, and
wherein the algorithm includes:
during each gait cycle, estimating from inertial signals received from at least one
6 degree of freedom inertial sensor 3D orientation, velocity, and trajectory of the foot, based on: temporal detection of cycles, knowledge of initial conditions of position and orientation, gravity cancellation of measured acceleration, and de-drifted integration of gravity-free acceleration; and
using the estimated 3D orientation, velocity, and trajectory of the foot in order to estimate gait parameters including stride length, foot clearance, stride velocity, and turning angle.

17. A method of 3D gait assessment, the method comprising:
obtaining, using at least one inertial sensor fixed to the foot or integrated on a shoe, a turning foot parameter and/or a clearance foot parameter, the clearance foot parameter being based on calculated heel clearance and toe clearance values; and
applying a sensor fusion and foot kinematics algorithm on the obtained parameter(s) in performing the 3D gait assessment,
wherein heel clearance (HC) and toe clearance (TC) values are calculated according to the following trigonometric relations:

$$HC = P_{sensor} + b - b*R_Z - a*R_X; \text{ and}$$

$$TC = P_{sensor} + b - b*R_Z + c*R_X,$$

where $P_{sensor}$ is sensor position, R is orientation, and {a, b, c} indicate relative position to heel and toe,
wherein at least one of a GPS receiver, force sensor, magnetometer, optical range sensor, and EMG electrode is synchronized with the at least one inertial sensor to provide extrinsic information.

* * * * *